(12) United States Patent
Alshehri et al.

(10) Patent No.: US 9,903,826 B2
(45) Date of Patent: Feb. 27, 2018

(54) MULTI-OBJECTIVE CORE-FLOOD TEST SYSTEM FOR OIL RECOVERY EVALUATION

(71) Applicants: Saudi Arabian Oil Company, Dhahran (SA); The Board of Trustees of the Leland Stanford Junior University, Stanford, CA (US)

(72) Inventors: Amar Jaber M. Alshehri, Khobar (SA); Anthony R. Kovscek, San Carlos, CA (US)

(73) Assignees: Saudi Arabian Oil Company, Dhahran (SA); The Board of Trustees of the Leland Stanford Junior University, Stanford, CA (US)

( * ) Notice: Subject to any disclaimer, the term of this patent is extended or adjusted under 35 U.S.C. 154(b) by 248 days.

(21) Appl. No.: 14/630,993

(22) Filed: Feb. 25, 2015

(65) Prior Publication Data
US 2016/0077023 A1   Mar. 17, 2016

Related U.S. Application Data

(60) Provisional application No. 62/051,444, filed on Sep. 17, 2014.

(51) Int. Cl.
| | | |
|---|---|---|
| *G01N 23/04* | (2006.01) | |
| *G01N 23/20* | (2018.01) | |
| *G01N 33/24* | (2006.01) | |

(52) U.S. Cl.
CPC ..... *G01N 23/046* (2013.01); *G01N 23/20025* (2013.01); *G01N 33/241* (2013.01); *G01N 2223/616* (2013.01)

(58) Field of Classification Search
CPC .......... G01N 23/046; G01N 23/20025; G01N 2223/616

(Continued)

(56) References Cited

U.S. PATENT DOCUMENTS

| | | | | |
|---|---|---|---|---|
| 4,583,242 A | * | 4/1986 | Vinegar ................. | G01N 33/24 378/20 |
| 4,669,299 A | * | 6/1987 | Closmann .............. | G01N 15/08 250/253 |

(Continued)

OTHER PUBLICATIONS

Kleppe et al., "Oil Production from Fractured Reservoirs by Water Displacement", SPE 5084, Copyright 1974, 20 pages.

(Continued)

*Primary Examiner* — Allen C. Ho
(74) *Attorney, Agent, or Firm* — Fish & Richardson P.C.

(57) ABSTRACT

Example methods and systems are described for performing core-flood tests for evaluating effectiveness of hydrocarbon recovery techniques. In some aspects, a core-flood test system includes a core holder configured to be coupled to a computed tomography (CT) scanner system to monitor fluid saturations of a core including a rock sample and a core sleeve to be received in the core holder. The core holder and the core sleeve are separated by a confining space. The core sleeve is configured to receive the core. The core sleeve is configured to contact the core in response to a confining pressure applied to the core sleeve in the confining space and to be separate from the core in response to the confining pressure being removed, creating a fracture space between the core and the core sleeve.

18 Claims, 15 Drawing Sheets

(58) Field of Classification Search
USPC .................................. 378/51–55, 57, 62, 208
See application file for complete search history.

(56) References Cited

U.S. PATENT DOCUMENTS

| | | | | |
|---|---|---|---|---|
| 4,688,238 | A * | 8/1987 | Sprunt | G01N 23/046 378/210 |
| 4,710,948 | A * | 12/1987 | Withjack | G01N 23/04 378/208 |
| 4,782,501 | A * | 11/1988 | Dixon, Jr. | G01N 15/088 250/253 |
| 4,799,382 | A | 1/1989 | Sprunt et al. | |
| 4,868,751 | A * | 9/1989 | Dogru | G01N 15/08 702/12 |
| 4,893,504 | A * | 1/1990 | O'Meara, Jr. | G01N 33/241 378/20 |
| 4,982,604 | A * | 1/1991 | Davis | G01N 33/241 324/376 |
| 5,023,895 | A * | 6/1991 | McCroskey | G01N 23/046 378/10 |
| 5,036,193 | A * | 7/1991 | Davis, Jr. | G01N 15/088 250/255 |
| 5,042,580 | A * | 8/1991 | Cullick | C09K 8/60 166/252.1 |
| 5,063,509 | A * | 11/1991 | Coles | G01N 23/046 250/269.1 |
| 5,086,643 | A * | 2/1992 | Marek | G01N 15/0826 73/38 |
| 5,109,398 | A * | 4/1992 | Hunt | G01N 15/082 250/253 |
| 5,164,590 | A * | 11/1992 | Coles | G01N 23/046 250/253 |
| 5,164,672 | A * | 11/1992 | Gilliland | G01N 33/241 250/255 |
| 5,297,420 | A | 3/1994 | Gilliland et al. | |
| 5,493,226 | A * | 2/1996 | Honarpour | G01N 33/241 324/376 |
| 5,698,772 | A | 12/1997 | Deruyter et al. | |
| 6,104,776 | A * | 8/2000 | Oikawa | G01N 23/06 378/10 |
| 6,178,807 | B1 * | 1/2001 | Baldwin | G01N 15/082 324/376 |
| 7,254,211 | B2 * | 8/2007 | Hunt | G01N 23/046 378/20 |
| 7,286,630 | B2 * | 10/2007 | Holt | A61B 6/032 378/20 |
| 7,775,715 | B2 * | 8/2010 | Warner | G01N 23/046 378/20 |
| 8,356,510 | B2 * | 1/2013 | Coenen | G01N 15/0806 73/38 |
| 8,657,000 | B2 | 2/2014 | Willingham et al. | |
| 8,725,477 | B2 * | 5/2014 | Zhang | E21B 49/00 703/10 |
| 9,261,435 | B2 * | 2/2016 | Collins | E21B 43/20 |
| 9,482,631 | B2 * | 11/2016 | Yang | G01N 24/081 |
| 2012/0241149 | A1 | 9/2012 | Chen et al. | |

OTHER PUBLICATIONS

Alshehri et al., "An X-Ray CT Study of Multidimensional Imbibition in Dual Porosity Carbonates", SPE 159423, Copyright 2012, 15 pages.
Mirzaei et al., "Visualization and Analysis of Surfactant Imbibition into Oil-Wet Fractured Cores", SPE 166129, Copyright 2013, 1 page.
Schembre et al., "Wettability Alteration and Oil Recovery by Water Imbibition at Elevated Temperatures", Supri TR-114 Report, Dec. 1998, 25 pages.
Standnes, "Enhanced Oil Recovery from Oil-Wet Carbonate Rock by Spontaneous Imbibition of Aqueous Surfactant Solutions", Department for Petroleum Technology, Stavanger, Sep. 17, 2001, 130 pages.
Takahashi, "Water Imbibition, Electrical Surface Forces, and Wettability of Low Permeability Fractured Porous Media", Sep. 2009, 228 pages.

* cited by examiner

MULTI-OBJECTIVE CORE-FLOOD TEST SYSTEM FOR OIL RECOVERY EVALUATION

CROSS-REFERENCE TO RELATED APPLICATIONS

This application claims the benefit of priority to U.S. Provisional Application Ser. No. 62/051,444, filed on Sep. 17, 2014, the contents of which are hereby incorporated by reference.

TECHNICAL FIELD

This disclosure relates to evaluating effectiveness of oil recovery techniques.

BACKGROUND

Hydrocarbon recovery is a process by which hydrocarbons are extracted from a subterranean region (e.g., a region from which heavy viscous oil or other hydrocarbons can be extracted, or other types of regions). Hydrocarbon recovery can include primary recovery, secondary recovery, and tertiary recovery (also referred to as enhanced oil recovery (EOR)). EOR generally includes techniques for increasing the amount of hydrocarbon production by altering a reservoir's rock properties and/or the in-situ fluid properties to mobilize the trapped oil in the subterranean region.

Water flood is an example secondary recovery method performed before EOR implementations, in which water is injected into the reservoir formation to displace residual oil. Water flood and primary recovery combined typically recover about 50% of the oil in place. This number is even lower in fractured reservoirs that account for more than 20% of the world's hydrocarbon reserves. Water injection can be problematic in fractured reservoirs because injectant selectively channels through fractures toward producers, leaving much oil behind in the matrix. Recovering retained oil requires advanced engineering and injecting sophisticated fluids to drive oil toward producers. Some main recovery mechanisms rely either on increasing the flow resistance of injectants in high-permeability fractures or improving the imbibition process in the matrix-fracture system.

SUMMARY

This disclosure describes systems and methods for performing core-flood tests for evaluating effectiveness of hydrocarbon recovery techniques. In general, example innovative aspects of the subject matter described here can be implemented as methods and systems for conducting core-flood tests for oil recovery evaluation.

In some aspects, one innovative aspect of the subject matter described here can be implemented as a system. The system can include a core holder configured to be coupled to a computed tomography (CT) scanner to monitor fluid saturations of a core including a rock sample and a core sleeve to be received in the core holder. The core holder and the core sleeve are separated by a confining space. The core sleeve is configured to receive the core. The core sleeve is configured to contact the core in response to a confining pressure applied to the core sleeve in the confining space and to be separate from the core in response to the confining pressure being removed, creating a fracture space between the core and the core sleeve.

This, and other aspects, can include one or more of the following features. The core is configured to receive injected hydrocarbon, and the system further includes an injection plate attached to a first end of the core holder for transferring injected fluids to the core and a production plate attached to a second end of the core holder for collecting at least a portion of the hydrocarbon produced from the core.

In some aspects, the system further includes multiple rods for connecting the injection plate, the production plate, and the core holder.

In some aspects, the system further includes sealants applied around an edge of the core sleeve in contact with the injection plate and an edge of the core sleeve in contact with the production plate.

In some aspects, the injection plate includes an injection end cap tapered to substantially match an inner diameter of the core sleeve for sealing the injection plate and the core sleeve.

In some aspects, the injection plate and the production plate each include a distribution channel for uniformly distributing injected fluids into the core. The distribution channel further includes an outer channel configured to transfer injected fluids to the fracture space between the core and the core sleeve.

In some aspects, the injection plate includes a first injection port for transferring an injection fluid into the core and a second injection port for transferring a confining fluid into the confining space.

In some aspects, the production plate includes a production port for transferring produced hydrocarbon.

In some aspects, the core includes carbonate.

In some aspects, the core holder is made of polyvinyl chloride (PVC).

In some aspects, the core holder is mounted substantially vertically for evaluating gravity effects on hydrocarbon recovery.

Another innovative aspect of the subject matter described here can be implemented as a method. A first core-flood test is performed on a core inside a core holder. A first set of computed tomography (CT) images of the core are collected while performing the first test. After performing the first core-flood test, a second core-flood test is performed on the core using the same core holder. A second set of CT images of the core are collected while performing the second core-flood test. Fluid saturations of the core are analyzed based on the first set of CT images and the second set of CT images.

This, and other aspects, can include one or more of the following features. The first core-flood test includes a saturation test and the second core-flood test includes an imbibition test.

In some aspects, prior to performing the first core-flood test, a CT image of the core is collected to calculate porosity of the core.

In some aspects, wherein performing a first core-flood test on a core includes, when the confining pressure is applied, injecting brine into the core and injecting a hydrocarbon fluid into the core.

In some aspects, $CO_2$ is injected into the core before injecting the brine into the core.

In some aspects, wherein performing a second core-flood test on the core includes, after releasing the confining pressure, injecting a hydrocarbon fluid into the fracture space between the core and the core sleeve; injecting brine into the core to mimic a water flood; and injecting a surfactant flood into the core.

A further innovative aspect of the subject matter described here can be implemented as a method. A first core-flood test of a core inside a core holder is performed, wherein the core holder is mounted in a horizontal orientation. A second core-flood test of the core inside the core holder is performed, wherein the core holder is mounted in a vertical orientation. A gravity effect on hydrocarbon production is evaluated based on a comparison of results of the first core-flood test and the second core-flood test.

This, and other aspects, can include one or more of the following features. Each of the first core-flood test and the second core-flood test comprises a saturation test and an imbibition test.

The details of these and other aspects and implementations of the present disclosure are set forth in the accompanying drawings and the description below. Other features and advantages of the disclosure will be apparent from the description and drawings.

BRIEF DESCRIPTION OF THE DRAWINGS

Like reference numbers and designations in the various drawings indicate like elements.

DETAILED DESCRIPTION

Figure 1:
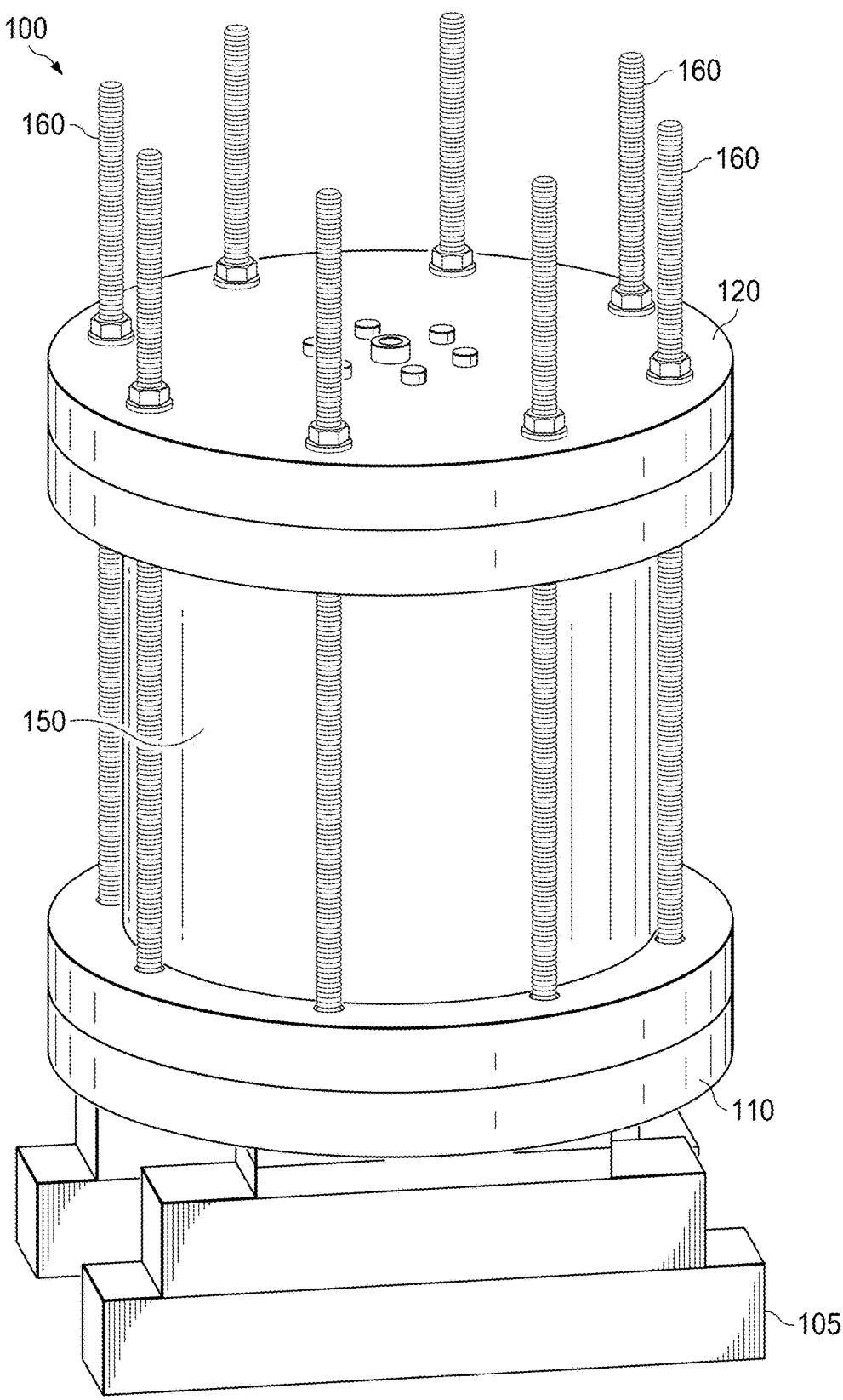
FIG. 1 is a schematic diagram showing an example core-flood test system.

This disclosure describes methods and systems for conducting core-flood tests, for evaluating effectiveness of hydrocarbon recovery techniques. For example, the methods and systems can be used to perform core-flood tests for evaluating the effects of fluids injection designed to improve hydrocarbon recovery from a subterranean region. A subterranean region can include a formation, a portion of a formation, or multiple formations. A subterranean region can contain hydrocarbons in its formation. Hydrocarbons can include oil, natural gas, or any mixtures of these and other hydrocarbons. Although this disclosure generally references "oil" recovery, the example techniques can be applied, adapted, or otherwise implemented to evaluate the effectiveness of recovery of other hydrocarbons from the subterranean region.

A core-flood test is a laboratory test in which a fluid or combination of fluids is injected into a core (e.g., sample of rock). The effects of the fluid injection on the core, such as permeability, relative permeability, saturation change, formation damage caused by the fluid injection, and/or interactions between the fluid and the rock, can be measured and their effects on oil recovery can be evaluated. The core-flood test can thus help design and optimize development options for an oil reservoir.

In some implementations, a core-flood test includes an imbibition process, a process of absorbing a wetting phase (e.g., water) into a porous rock. Imbibition processes can be classified into forced imbibition and spontaneous imbibition, which refer to the process of absorption with and without pressure driving the wetting phase into the rock, respectively. Improving the imbibition process is an example technique for increasing the flow resistance, and thus improving the oil recovery.

The example system described herein for performing core-flood tests (also referred to as core-flood test system) can include, among other things, a core, a core sleeve, a core holder, an injection plate, and a production plate. The example system can include or otherwise be coupled with an X-ray computed tomography (CT) scanner system. The CT scanner system can include a CT scanner for scanning tomography and recording CT images/scans and a computer system for post-processing of the CT images. Example post-processing can include measuring and analyzing porosity, quantifying fluid saturations, monitoring front movements in the core, calculating recovery factors, or other types of analyses for evaluating effectiveness of hydrocarbon recovery techniques. For accurate saturation measurements, the experiments are conducted in the CT scanner system from beginning to end. Positioning errors in X-ray CT scanning are usually observed in the subtraction calculation in the image analysis. The porosity and saturation calculations require subtracting CT images that are scanned at the same location. Thus, the core-flood test system is aligned in the gantry for every scan. In some instances, the core-flood test system to be scanned can be either stationary or be connected to a positioning system throughout the experiment.

The example methods and systems allow for conducting a saturation test and an imbibition test of the core (and cleaning the core) within the same system while the system is mounted to the X-ray CT scanner positioning table. The example methods and systems can provide X-ray CT imaging of in-situ fluid distribution within the core. Compared to existing systems using two core holders or two systems for saturating the core and conducting an imbibition experiment with the X-ray CT scanner, the example systems described here achieve both objectives and reduce or eliminate positioning errors resulting from replacing the core holder.

In some implementations, the core used by the example core-flood test systems can be made of carbonates, sandstones, or other types of rock materials. Working with carbonates is challenging because of the complexity that arises from the variation of pore sizes (macroporosity and microporosity), pore shapes, and pore interconnectivity. In some implementations, the example methods and systems can be used for core-flood tests on carbonates, particularly for evaluating the effects of fluid injection on oil recovery in a fractured carbonate formation.

The example system can be used for conducting a core-flood test in a horizontal, vertical, or another orientation. In some implementations, the example method can include performing both a horizontal core-flood experiment and a vertical core-flood experiment. As such, the example method can evaluate the effects of gravity forces on oil recovery by comparing the vertical core-flood experiment with the horizontal core-flood experiment.

In some implementations, each of the two core-flood experiments can include two tests (or phases): a saturation test and an imbibition test. In the saturation test, a confining pressure is applied while saturating the core with brine followed by oil. After obtaining initial water and oil saturations, the confining pressure is released. By doing so, an annular space is created by the core and the sleeve. This space mimics a fracture surrounding the core. The imbibition test then starts, during which injected fluids can selectively channel through the fractures towards the outlet, and oil recovery from the matrix becomes mainly governed by spontaneous imbibition.

In some implementations, the example methods and systems allow conducting core-flood experiments with a surrounding fracture without the need for inducing a fracture or damaging the core. The example methods and systems can allow easy and convenient implementation of quantifying fluid saturations locally within the core, cleaning the core, and starting a new experiment. In some implementations, the example methods and systems enable evaluating gravity effects on oil recovery of fractured systems, for example, by mounting the system vertically and comparing the vertical system setup with the horizontal system setup. In some implementations, the example methods and systems can investigate the improvement of oil recovery in fractured carbonates at low interfacial tensions (IFT) between oil and aqueous phases while accounting for gravitational effects. The systems can be cost-effectively manufactured, for example, in a machine shop. In some implementations, the core holder can be designed, customized, and fabricated for different cores or specific applications. The dimensions and specifications of the systems can be designed, optimized, or otherwise configured accordingly. Additional or different features or advantages can be achieved in some implementations.

FIG. 1 is a schematic diagram showing an example core-flood test system 100. The example core-flood test system 100 includes an injection plate 110, a production plate 120, a core holder 150, and multiple rods 160. The example core-flood test system 100 can further include or sit on a base 105 (e.g., elevating blocks), for example, to facilitate the example core-flood test system 100 to be connected to one or more of a tubing (e.g., an injection tube 115, confining tube 225), or other peripheral components or devices. The example core-flood test system 100 can include or is otherwise coupled to a CT scanner system (not shown). For example, the core holder 150 can be mounted horizontally, vertically, or at an arbitrary angle (e.g., from 0° to 90°) relative to the horizontal axis on a positioning system of a CT scanner system.

Figure 2:
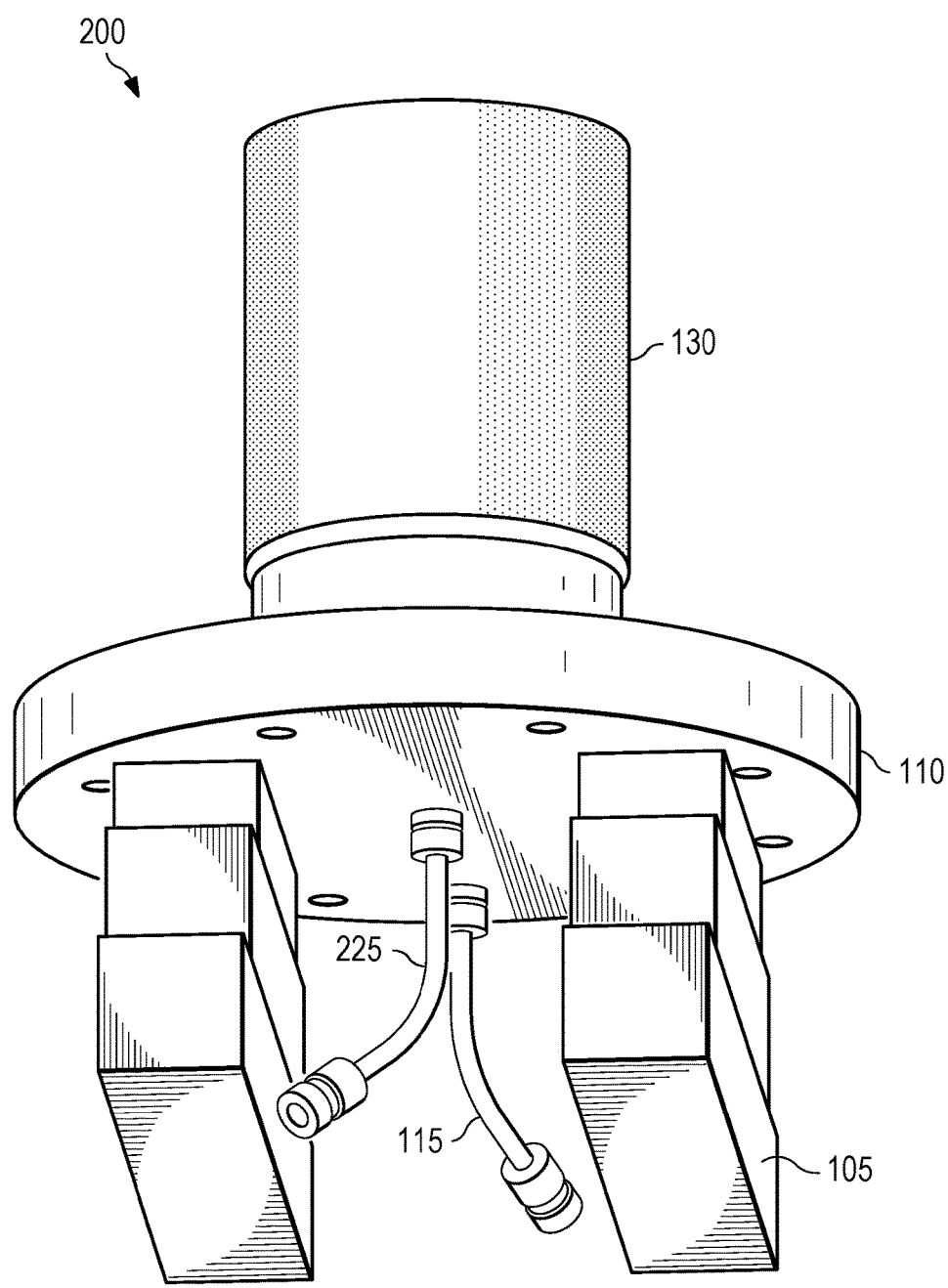
FIGS. 2-8 are schematic diagrams showing components of an example core-flood test system shown at different stages of an example assembling process of the example core-flood test system.

FIGS. 2-8 are schematic diagrams 200-800 showing different stages of an example assembling process of the example core-flood test system 100. For example, FIG. 2 is schematic diagram 200 showing a core 130 placed on top of the injection plate 110 after connecting the injection plate 110 to the injection tube 115 and the confining tube 225. The injection plate 110 is placed on the base 105. The core 130 can include a rock sample and/or sand packs of a particular formation or reservoir of interest. For instance, the core 130 can be a carbonate core (e.g., a Texas cream core or an oil field core).

Figure 3:
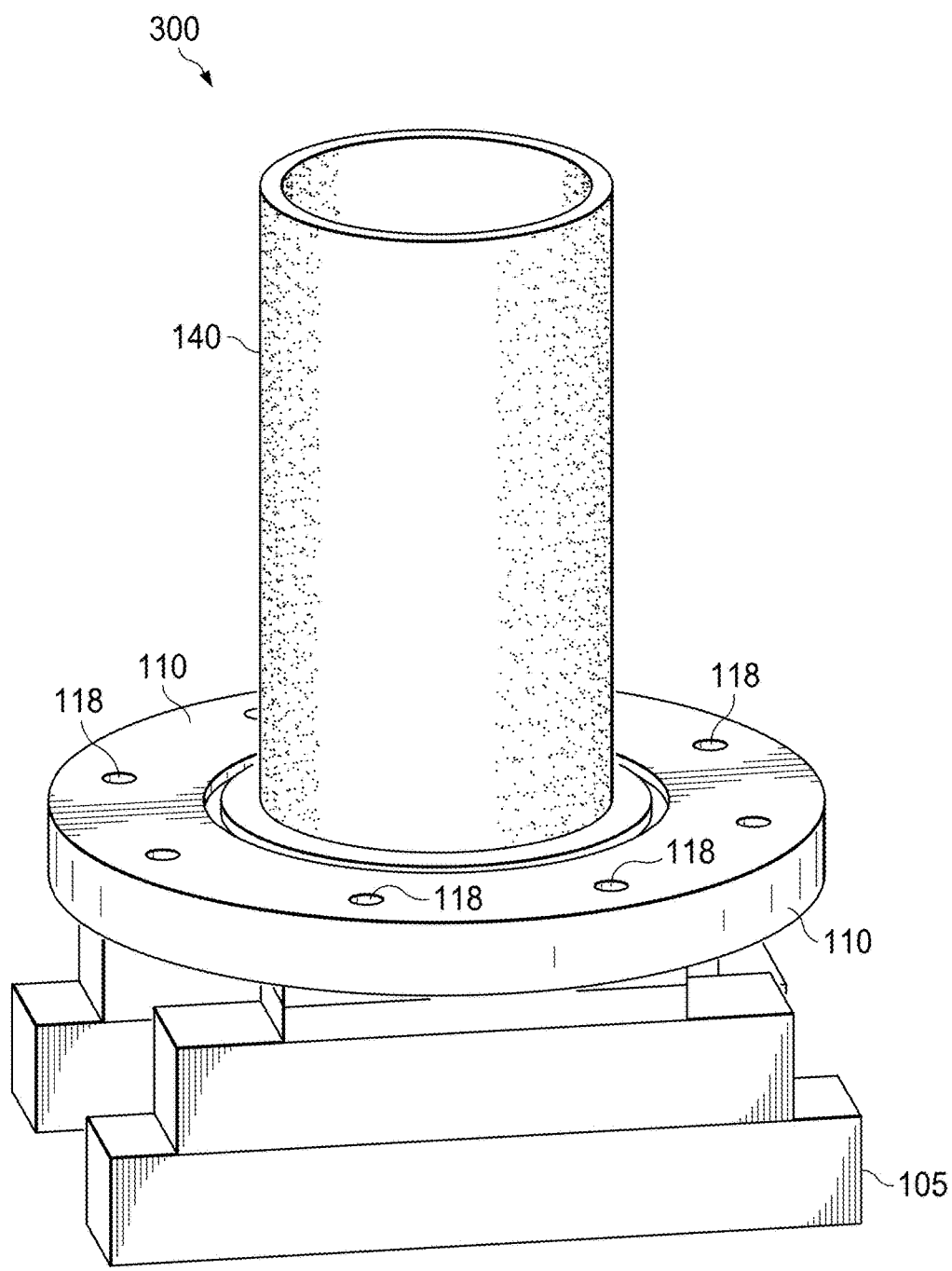

FIG. 3 is schematic diagram 300 showing a core sleeve 140 that is inserted around the core 130 into the injection plate 110. The core sleeve 140 can be made of polyvinyl chloride (PVC) or another material that is penetrable by X-rays and can handle the confining pressure. The core sleeve 140 can be a tube or another shape configured to receive and house the core 130.

Figure 4:
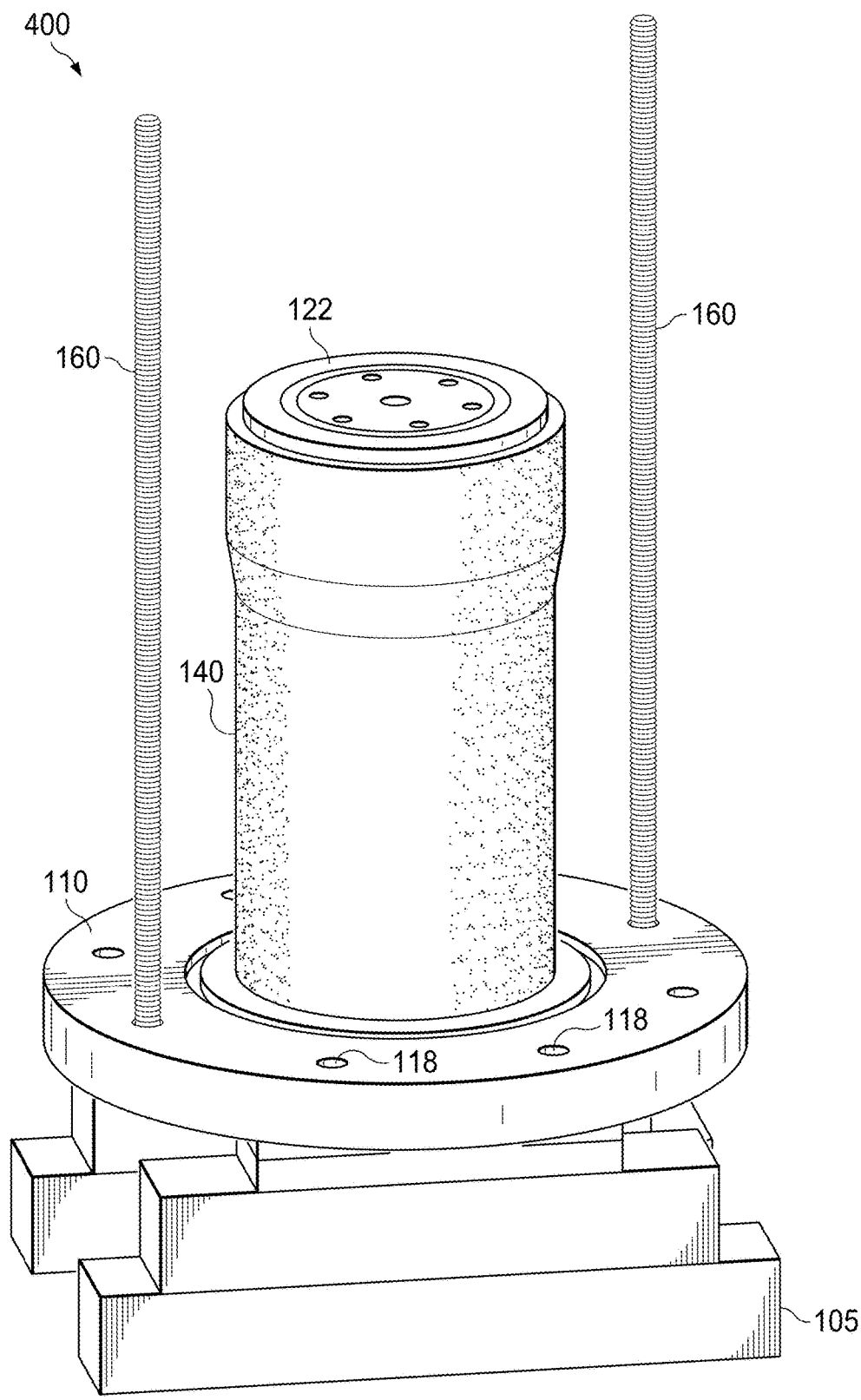

FIG. 4 is a schematic diagram 400 showing a production end cap 122 that is placed on top of core 130 through the core sleeve 140. The production end cap 122 can be a part of the production plate 120. FIG. 4 also shows multiple slots 118 machined into the injection plate 110 to receive the multiple rods 160 for connecting the injection plate 110, the core holder 150, and the production plate 120. As shown in FIG. 4, two rods 160 are inserted into two respective slots 118. The multiple rods 160 can be made of aluminum or another material. The multiple rods 160 in FIGS. 1-8 have a length of 9.525 mm.

Figure 5:
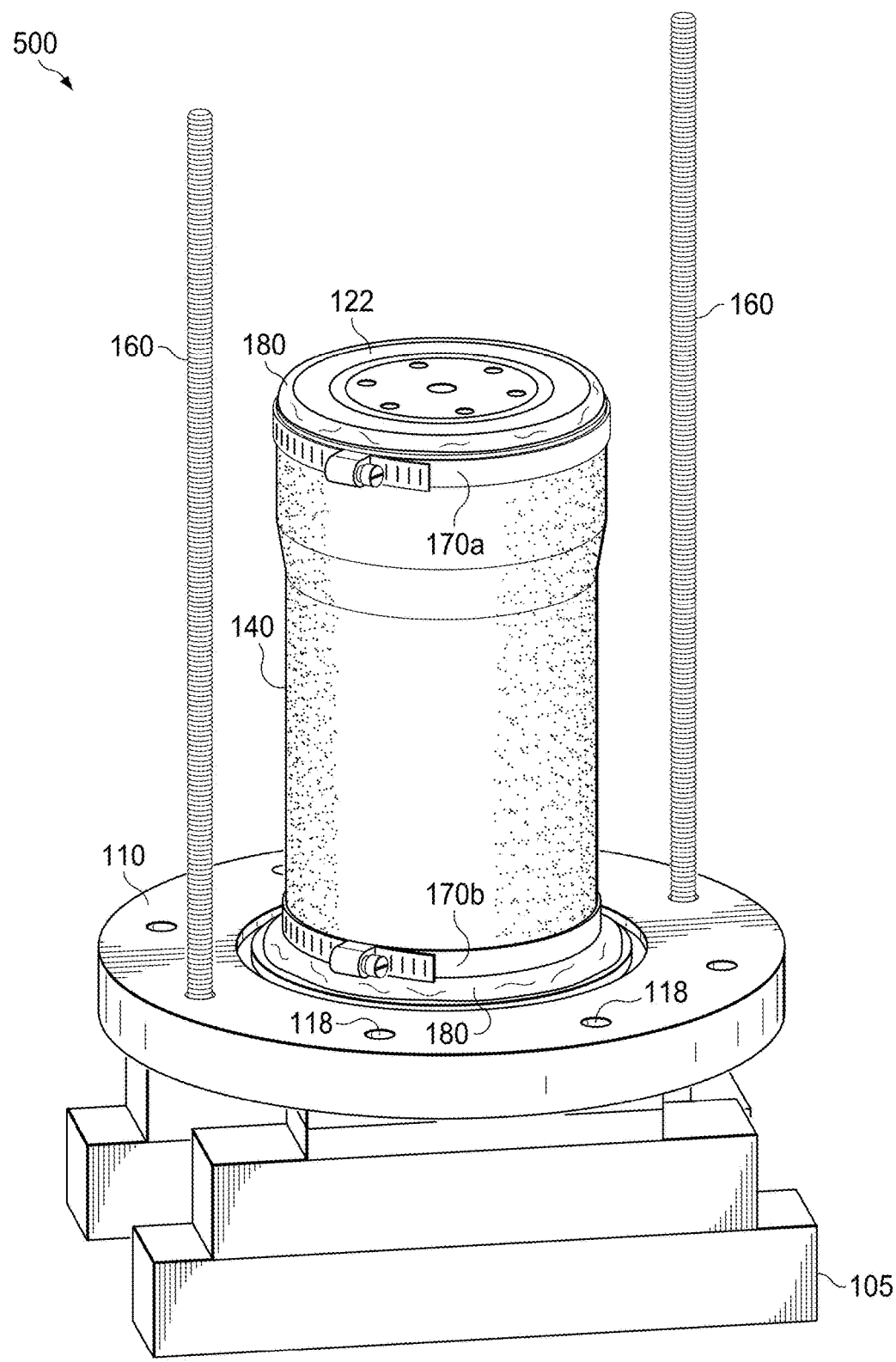

FIG. 5 is a schematic diagram 500 showing two hose clamps 170a and 170b that are gently tightened at the two ends of the core sleeve 140. Solvent-resistant sealants 180 (e.g., Dow Corning 730) can be applied to the edges of the core sleeve 140 as another barrier between the confining fluid and the inside of the core sleeve 140 to avoid leakage.

Figure 6:
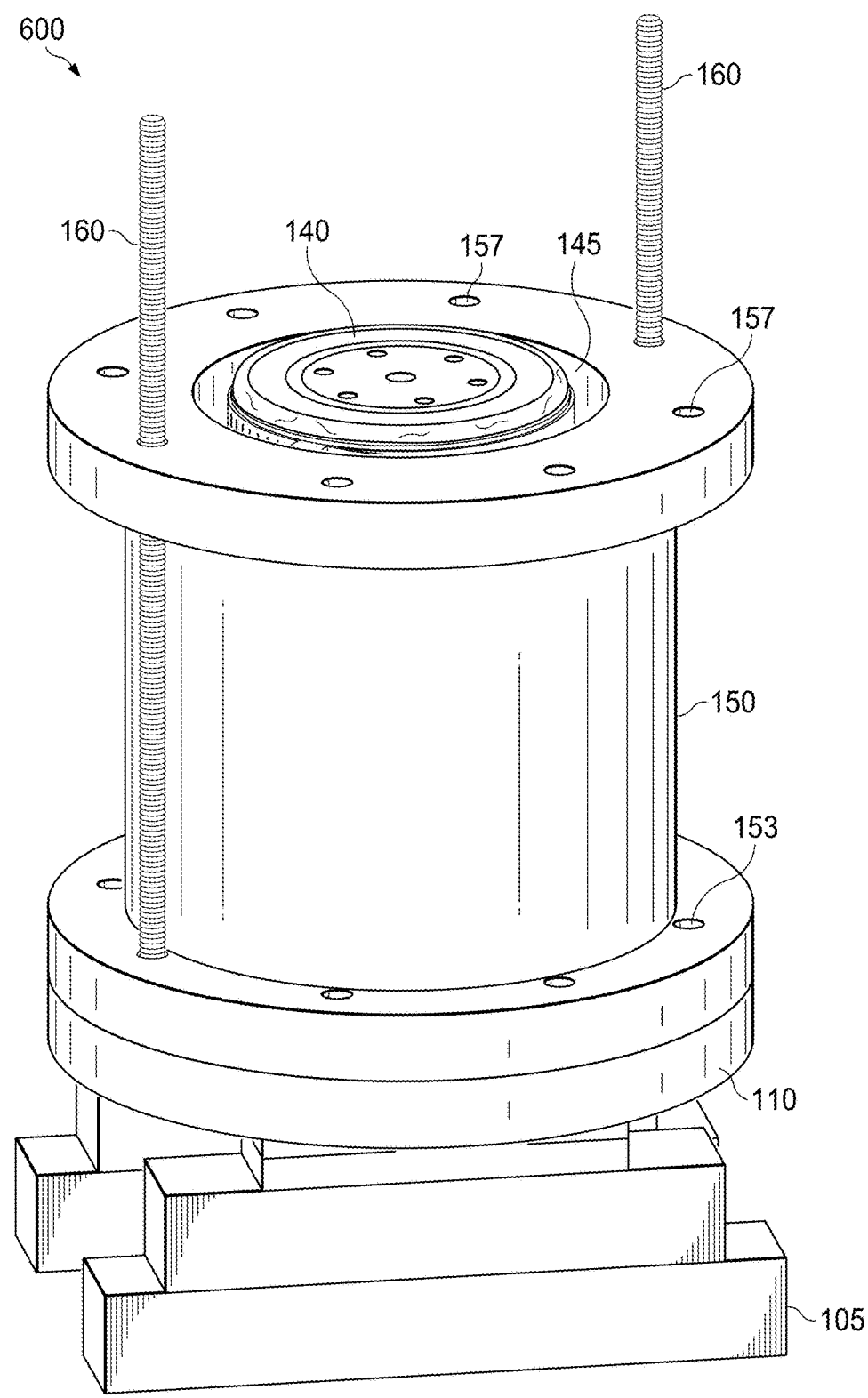

FIG. 6 is a schematic diagram 600 showing the core holder 150 placed on top of the injection plate 110 and around the core sleeve 140. The core holder 150 and the core sleeve 140 are separated by a confining space 145, for example, for receiving confining fluid to apply confining pressure to the core sleeve 140. The core holder 150 can be a PVC tube or can be made of another material or in another shape. Two aluminum rods 160 are inserted into the respective slots of the injection plate 110 for alignment of the core holder 150 and the injection plate 110.

Figure 7:
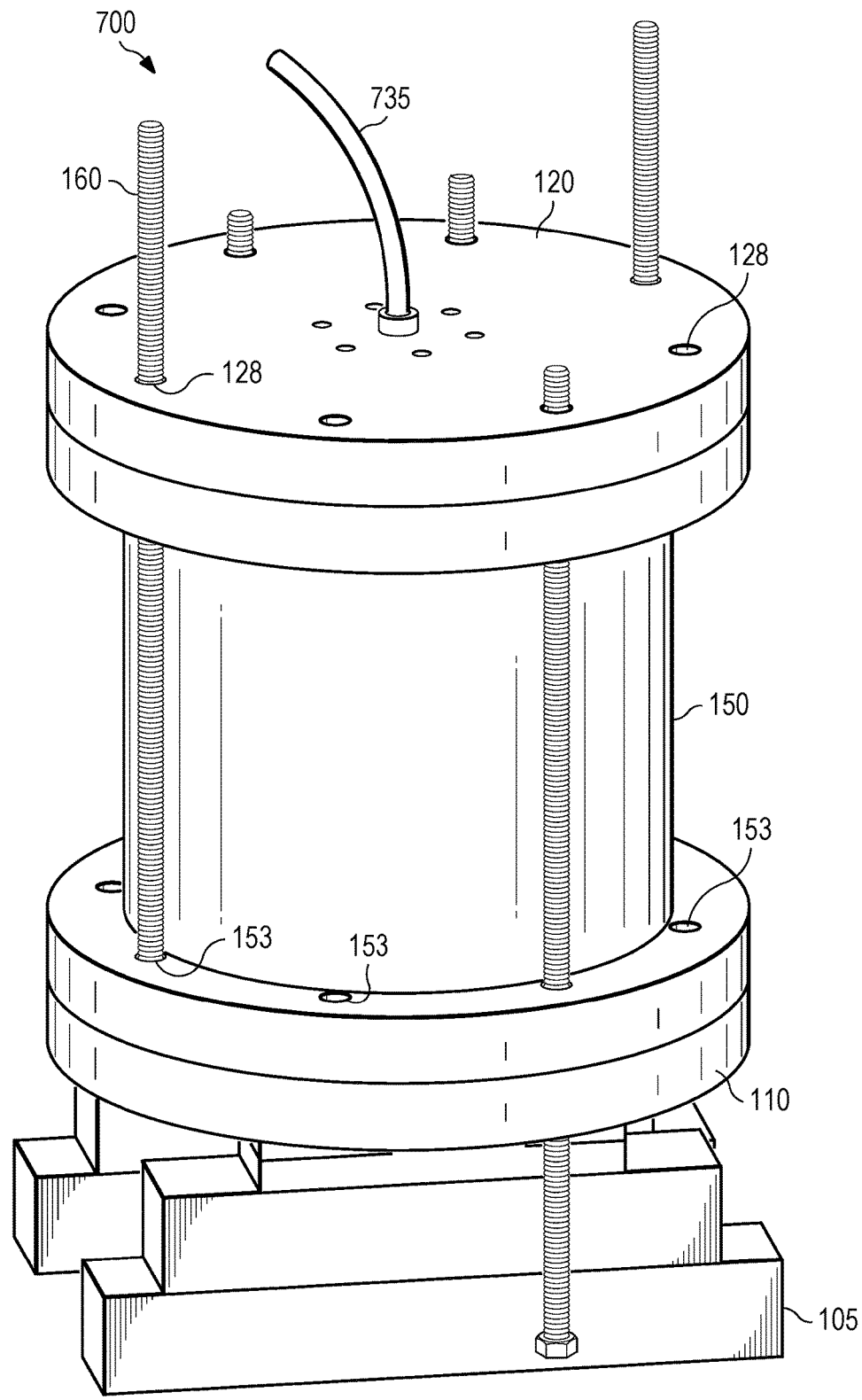

FIG. 7 is a schematic diagram 700 showing the production plate 120 placed on top of the production end cap 122. A production tube 735 is connected to the production end cap 122 for transferring produced hydrocarbon. Four aluminum rods 160 are inserted into the slots 128 on the production plate 120, extending through the respective slots 153 of the core holder 150 and slots 118 (not shown) of the injection plate 110. As such, the production plate 120 is attached to and aligned with the core holder 150 and the injection plate 110 using multiple rods 160.

Figure 8:
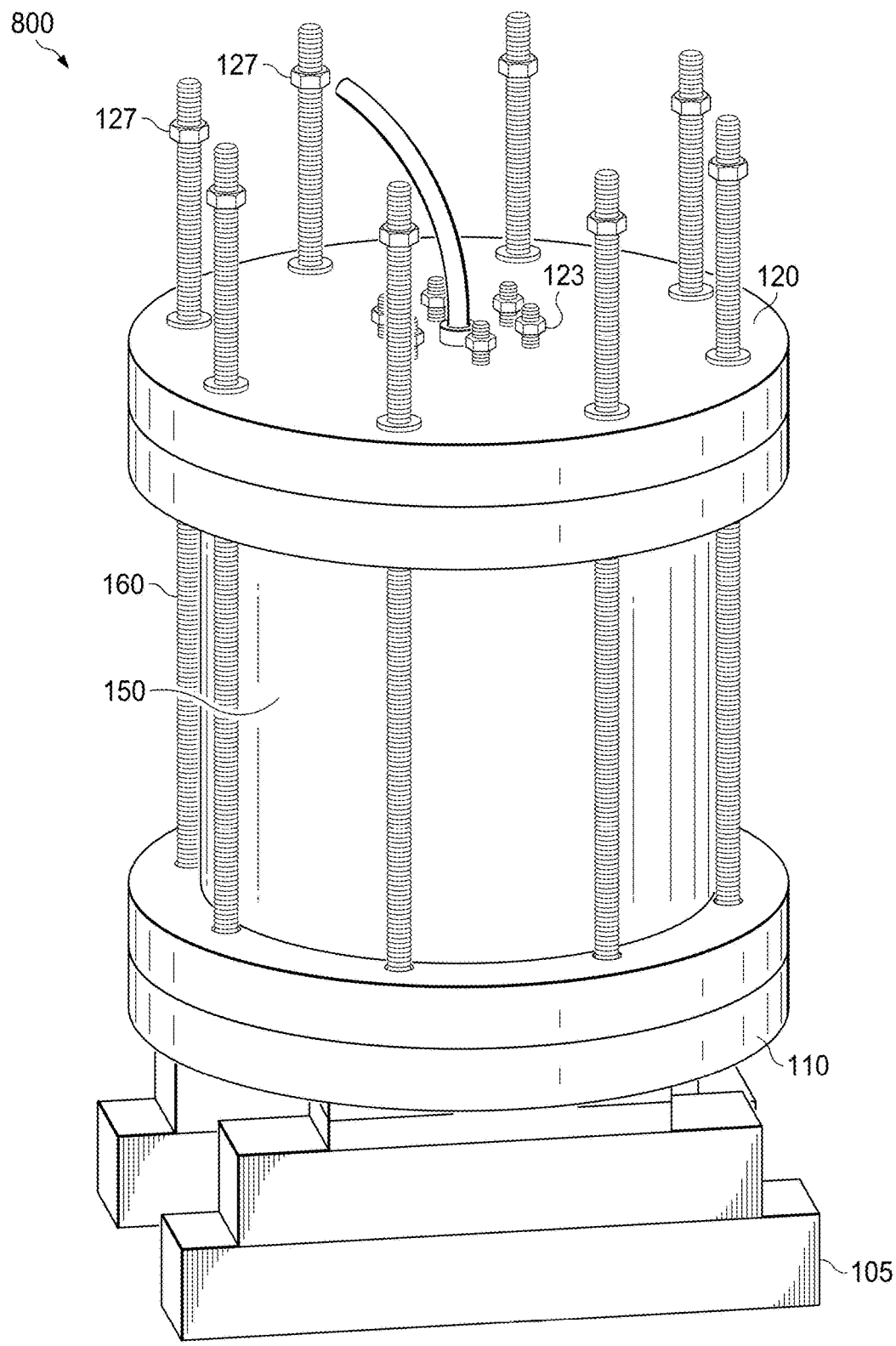

FIG. 8 is a schematic diagram 800 showing the example core-flood test system 100 with eight rods 160 inserted for connecting and aligning the injection plate 110, the core holder 150, and the production plate 120. Washers and nuts 127 can be used from both the top side of the production plate 120 and the bottom side of the injection plate 110 for fastening the eight rods 160. Screws 123 can be used to hold the production end cap 122 and the production plate 120.

Figure 9B:
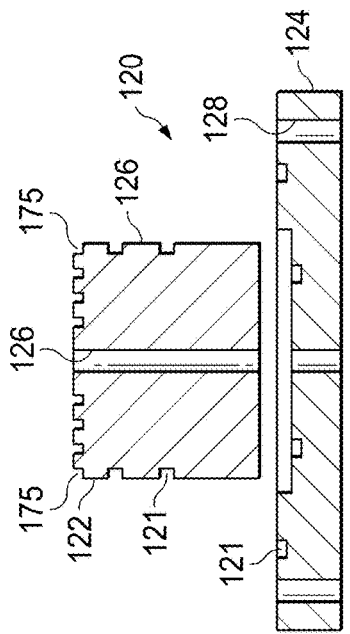
FIG. 9B is a schematic diagram showing a cross-sectional view of a production plate of the example core-flood test system.
Figure 9A:
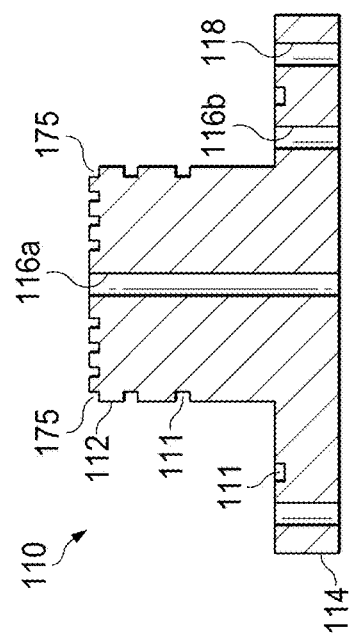
FIG. 9A is a schematic diagram showing a cross-sectional view of an injection plate of the example core-flood test system.

FIG. 9A is a schematic diagram showing a cross-sectional view of the injection plate 110 of the example core-flood test system 100. As illustrated, the injection plate 110 includes an injection end cap 112 and an injection base plate 114. The injection end cap 112 is tapered to substantially match the inner diameter (ID) of the core sleeve 140 for better sealing between the injection plate 110 and the core sleeve 140 (see FIG. 3).

The injection plate 110 has two injection ports 116a and 116b. A first injection port 116a, extending longitudinally through the injection base plate 114 and the injection end cap 112, is configured to transfer injection fluid into the core 130. The first injection port 116a is connected to the injection tube 115 (see FIG. 2). A second injection port 116b, extending longitudinally through the injection base plate 114, is configured to transfer confining fluid into the confining space 145 between the core sleeve 140 and the core holder 150 (see FIG. 6). FIG. 9A also shows the multiple slots 118 of the injection plate 110 for passing through the multiple rods 160.

FIG. 9B is a schematic diagram showing a cross-sectional view of the production plate 120 of the example core-flood test system 100. As illustrated, the production plate 120 includes the production end cap 122 and a production base plate 124. In some implementations, the production end cap 122 is attached to the production base plate 124 using six 2¼×1½ inch socket cap screws (not shown). An O-ring (e.g., 70 Buna size 234, not shown) can be used to seal between the production end cap 122 and the production base plate 124.

The production end cap 122 is tampered to substantially match the inner diameter (ID) of the core sleeve 140 for better sealing between the injection plate 110 and the core sleeve 140 (see FIG. 4). The production base plate 124 is similar to the injection plate 114 except that it does not have a port for the confining fluid. The production base plate 124 includes a production port 126 for transferring produced hydrocarbon. The production port 126 can be connected to a production tube (e.g., the production tube 735 as shown in FIG. 7).

In some implementations, the injection plate 110 and production plate 120 (including the end caps 112 and 122) can be made of stainless steel or other materials so as to handle the confining pressure. The injection plate 110 and the production plate 120 can include multiple O-ring groves 111 and 121 such that O-rings can be used on each plate to avoid fluid leakage from the confining space 145 to the atmosphere. Example specifications of the O-rings include V2-258 5.984 in (outer diameter, "OD")×0.139 in (W) and V2-342 4.020 in (OD)×0.210 in (W). Additional or different specifications can be used.

Figure 9D:
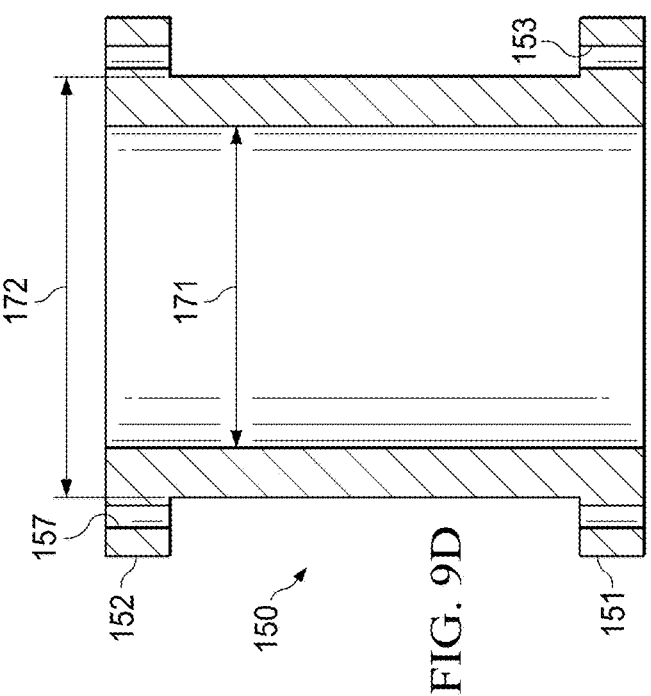
FIG. 9D is a schematic diagram showing a cross-sectional view of a core holder of the example core-flood test system.
Figure 9C:
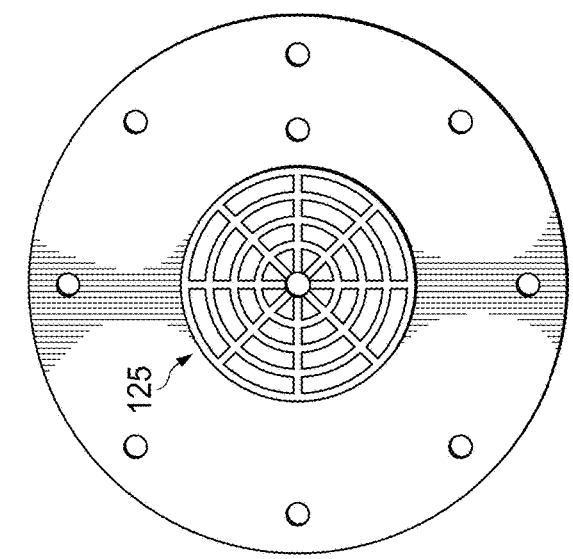
FIG. 9C is a schematic diagram showing a top view of an example distribution channel.

FIG. 9C is a schematic diagram showing a top view of an example distribution channel 125. The distribution channel 125 can be machined on the injection end cap 112 and the production end cap 122. The injection end cap 112 and the production end cap 122 can have the same, similar, or different distribution channels. The core 130 is placed between the injection end cap 112 and the production end cap 122. Fluids can flow through the distribution channel 125 into and out of the core 130. The example distribution channel 125 shown in FIG. 9C has a spider-web pattern to allow a uniform distribution of fluids to the adjacent faces of the core 130. Additional or different patterns can be used. More importantly, the distribution channel 125 has an outer channel 175 (see FIGS. 9A and 9B) that allows conveying the injected fluid to the fracture-like space 135 around the core 130 when no confining pressure is applied.

FIG. 9D is a schematic diagram showing a cross-sectional view of the example core holder 150 of the example core-flood test system 100. The example core holder 150 can be a tube or another shape. The example core holder 150 has a first end 151 to be attached to the injection plate 110 and a second end 152 to be attached to the production plate 120, through the multiple rods 160. The first end 151 and the second end 152 include respective slots 153 and 157 to receive the multiple rods 160 for fastening the core holder 150 with the injection plate 110 and the production plate 120.

The example core holder 150 is configured to house the core sleeve 140 and the core 130. Specially, a confining space (the confining space 145 as shown in FIG. 6) exists between the core holder 150 and the core sleeve 140. For instance, the example core holder 150 has an OD 172 of 8⅝ in and an ID 171 of 5¾ in, while the core sleeve 140 has an OD of 4.2175 in and an ID of 4.03 in (e.g., Viton 70 durometer 3/16 in (wall)). Thus, an annulus confining space is formed around the core sleeve 140.

In some implementations, the core holder 150 is made of polyvinyl chloride (PVC). The PVC tube (e.g., PVC Type I) has a tensile strength of 7500 psi. In some implementations, the confining pressure should be greater than the injection pressure by 300 psi to ensure adequate confinement of the sleeve around the core 130. Assume that the injection pressure is 200 psi leading to a confining pressure of 500 psi. Hoop stress calculations can be performed to evaluate the integrity of the core holder 150 under the experiment's conditions. The hoop stress at a confining pressure of 500 psi is about 1300 psi, which is less than the tensile strength of PVC by a factor of five. Thus, the PVC tube can handle the confining pressure.

Figure 10:
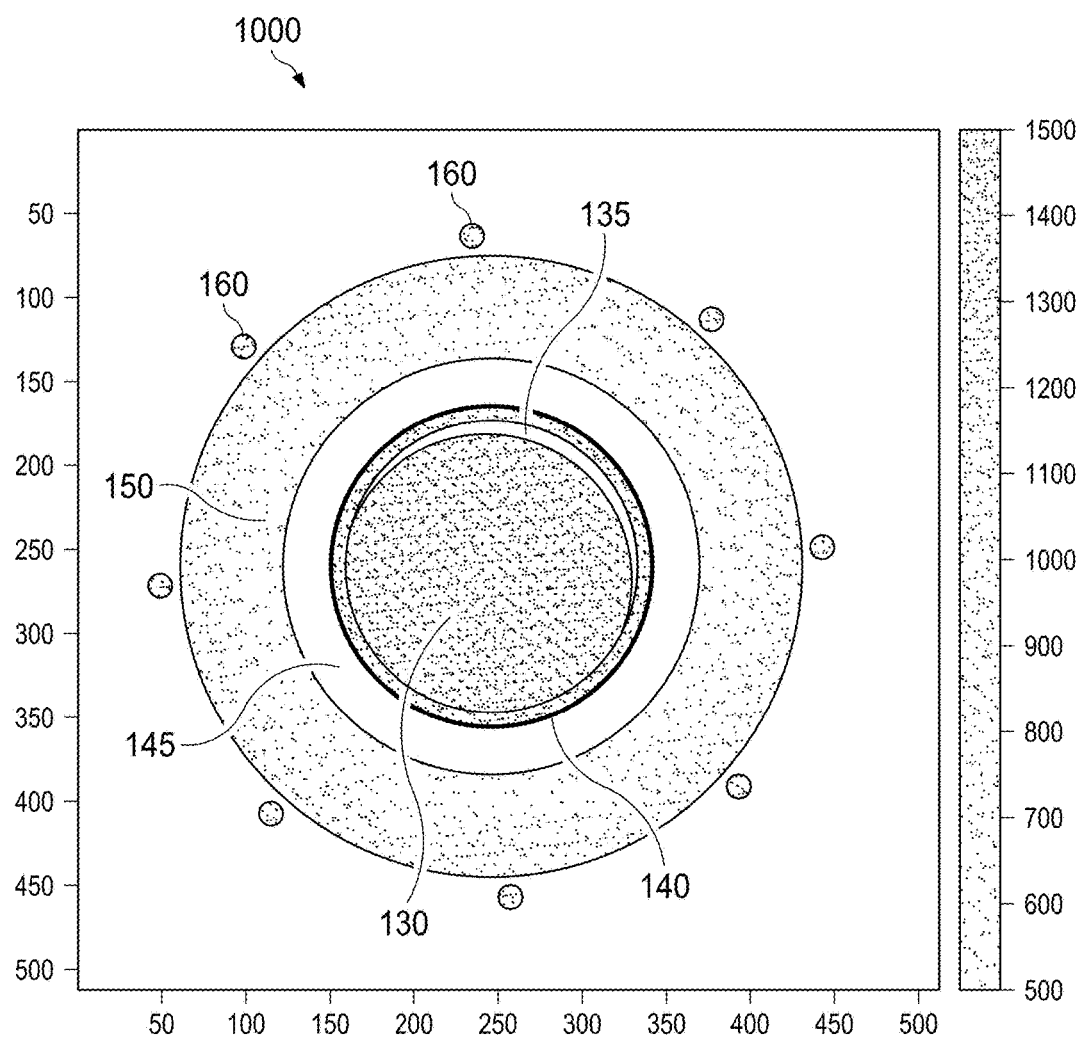
FIG. 10 is a schematic diagram showing a cross-sectional view of an example core-flood test system.

FIG. 10 is a schematic diagram showing a cross-sectional view 1000 obtained from an X-ray CT image of the example core-flood test system 100. As shown in FIG. 10, the core 130 is surrounded by the core sleeve 140 in the core holder 150. An annulus confining space 145 is formed between the core sleeve 140 and the core holder 150 where the confining fluid can be injected to apply confining pressure onto the core sleeve 140. After the confining pressure is released, a fracture-like space 135 is formed in the annulus between the core 130 and the core sleeve 140. The fracture aperture around the core 130 is half the difference of the ID of the core sleeve 140 and the OD of the core 130. For example, given the core's OD of 4 in and the core sleeve's ID of 4.03 in, the fracture aperture is 0.015 in ((4.03 in −4.00 in)/2). As such, the example core-flood test system 100 allows conducting imbibition tests in fractured media without the need of inducing a fracture in the core 130. In other words, the core holder 150 allows for a non-destructive method to conduct imbibition experiments. The core holder 150 also allows conducting the saturation test and imbibition test of the core 130 within a single system setup. By doing that, the saturation test and imbibition test can be scanned by an X-ray CT scanner system from beginning to end, reducing or eliminating positioning error. Thus, the example core-flood test system 100 can provide accurate CT responses and imaging by the X-ray CT scanner system.

Figure 11:
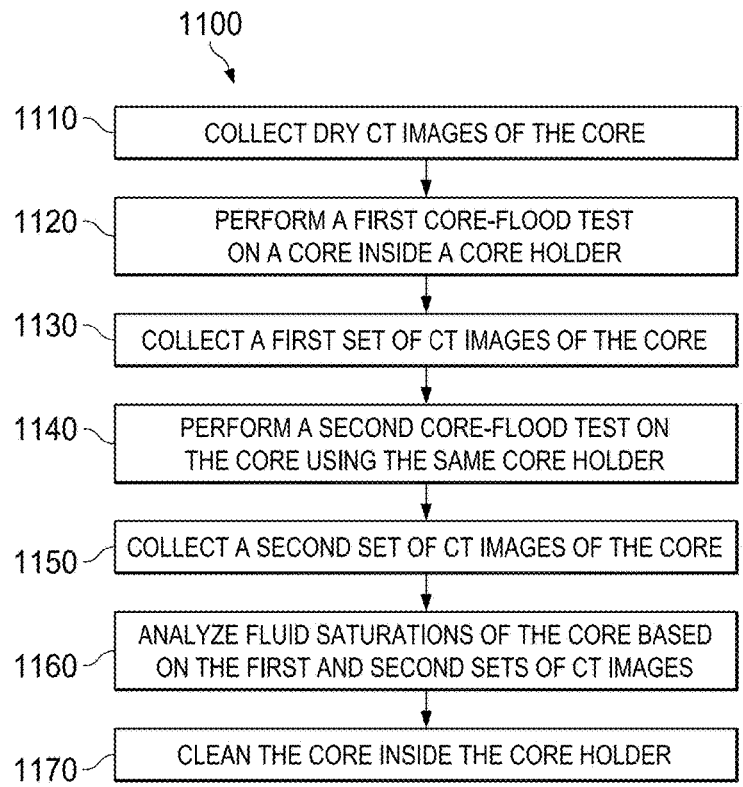
FIG. 11 is a flow chart of an example method for operating an example core-flood test system.

FIG. 11 is a flow chart showing an example process 1100 for operating the example core-flood test system 100, for example, to analyze fluid saturations of the core 130 and evaluate different oil recovery techniques. As described above, the example core-flood test system 100 includes or is otherwise coupled to an X-ray CT scanner system. X-ray CT scanners have been used in petroleum engineering research as a non-destructive tool to measure porosity and fluid saturations in a core 130. CT scanning involves measuring the attenuation of an X-ray beam that incrementally rotates around an object at a single plane. The measured attenuations are inputted into back projection algorithms utilizing Fourier transform functions. The final result of CT scanning is a cross-sectional image (2D) of CT numbers along the scanned plane averaged over the desired thickness (e.g., 3 mm). Eventually, CT provides 2D images with a fine resolution on the millimeter scale; 3-dimensional (3D) images are obtained by interpolating the 2D images.

Calculations of local porosity and fluid saturations are possible from the CT measurements. The analogy of the calculations is based on subtraction. The CT response for a saturated core, for example, is attributed to the rock and the saturating fluid. Porosity (Φ) can be calculated by subtracting two CT scans or images of a core 130 fully saturated with two different fluids, e.g., air and water as:

$$\phi = \frac{CT_{wr} - CT_{ar}}{CT_w - CT_a} \quad (1)$$

where CT represents CT numbers with a dimensionless unit of Hounsfield (H). High density matters have high CT numbers. The subscripts w and a correspond to water and air, respectively. The subscript r corresponds to a rock (core) saturated with a fluid. It is seen from Eq. (1) that the calculated porosity using X-ray CT scanning is the effective porosity. Pores that are not invaded by water (or the injected phase) will not be accounted for in Eq. (1).

Oil saturation ($S_o$, the subscript o refers to oil) can be found using Eq. (2):

$$S_o = \frac{CT_{wr} - CT_{owr}}{CT_{wr} - CT_{or}} \quad (2)$$

where $$CT_{owr} = (1-\Phi)\mu_r + \Phi S_o \mu_o + \Phi S_w \mu_w \quad (3)$$

and $$CT_{or} = CT_{dry} \frac{CT_o - CT_a}{CT_w - CT_a}(CT_{wr} - CT_{dry}) \quad (4)$$

where μ represents linear attenuation coefficient.

Oil saturation ($S_o$) can also found by the following formulation:

$$S_o = \frac{CT_{owr} - CT_{wr}}{CT_o - CT_w} \quad (5)$$

Note that the porosity and saturation calculations are performed at the elemental volume (voxel) level. The numerator involves subtracting two images scanned at the same location. The denominator involves the difference between the fluid pair used in the experiment with the addition of the voxel porosity in the saturation calculation.

At 1110, CT images of the core 130 are collected before saturating the core. In some implementations, the core 130 can be vacuumed to dry the core 130 from any moisture. The CT scanner system can scan the dry core 130 to obtain one or more CT images of the dry core 130 (also referred to dry images or dry scans). For example, the dry scans of the core 130 can be collected inside the core holder 150. The dry scans can be used for calculating porosity of the core 130.

At 1120, a first core-flood test is performed on the core 130 inside the core holder 150. The first core-flood test can include a saturation test (also referred to as a saturation phase). In some implementations, to saturate the core 130, confining pressure can be applied to the core sleeve 140 and thus to the core 130. For example, nitrogen can be used as the confining fluid at a pressure of 500 psi. The confining fluid can be injected, for example, through the confining tube 225 and the second injection port 116b of the injection plate 110 into the confining space 145. Confining the core ensures that the injected fluids (e.g., brine) are forcibly imbibed into the core 130. In some implementations, performing a first core-flood test includes, when the confining pressure is applied, injecting an injection fluid (e.g., brine) into the core; injecting a hydrocarbon fluid (e.g., decane, crude oil, etc.) into the core; collecting CT images of the core during the saturation test; and obtaining a first hydrocarbon saturation of the core. In some implementations, CO2 is injected into the core 130 before brine is injected because CO2 is more soluble in brine as compared to air so that it eases saturating the core 130 with brine.

In some implementations, after the brine injection, sodium bromide (NaBr) can be added to the brine at a 5% wt concentration. This brine with the 5% NaBr will be referred to as NaBr brine. The addition of NaBr can enhance the CT contrast between the brine and decane that will be injected afterwards. After the NaBr brine injection, decane, as an example hydrocarbon fluid, can be injected into the core 130 to obtain an initial oil saturation. In some implementations, the hydrocarbon fluid can include additional or different types of hydrocarbon. For example, decane is used as the oil phase rather than crude oil to focus the study on fluid-fluid interactions and minimize fluid-solid interactions. In some instances, light crude oil (e.g., 34° API) is also used to not only capture fluid-fluid but also fluid-rock interactions.

At 1130, a first set of computed tomography (CT) images of the core 130 are collected while performing the first test. For example, the CT scanner system can scan the saturated core 130 during the brine saturation phase to obtain one or more CT images of the core 130 that is fully saturated with brine (also referred to fully saturated brine scans). As such, porosity calculation can be performed using the dry scan and the fully saturated brine scan as described by Eq. (1). The CT scanner system can also monitor or scan the core 130 during the oil saturation phase to obtain one or more CT images of the core 130 that is saturated with oil to obtain an initial oil saturation.

FIGS. 12A-F are example 3D CT images showing decane saturation history of a core during a saturation test. The example saturation test includes a decane injection from the top of the core 130. The pore volume injected (PVI) at different stages of the saturation test are recorded. As shown from FIG. 12A to FIG. 12F, decane moves with a clear front through the core 130.

After saturating the core 130 and obtaining the initial oil saturation, the confining pressure is released, which relaxes the core sleeve 140, rendering a fracture space 135 around the core 130 that mimics a fracture surrounding the core 130. The injected fluid can selectively channel through the surrounding fracture space 135 to the production port 126. Accordingly, the imbibition test (or the imbibition phase) starts.

At 1140, after performing the first core-flood test, a second core-flood test is performed on the core 130 using the same core holder 150. In some implementations, the second core-flood test includes an imbibition test. In some implementations, performing a second core-flood test on the core 130 includes, after releasing the confining pressure, injecting a hydrocarbon fluid into the fracture space 135 between the core 130 and the core sleeve 140; injecting brine into the core 130 to mimic a water flood; and injecting a surfactant flood into the core 130. For example, as the core sleeve 140 opens up in response to the removal of the confining pressure, decane injection can be resumed to fill the fracture space 135. After that, NaBr brine can be used as the water flood while the NaBr brine, a surfactant, and an alkali can be used as the surfactant flood. The water flood can include additional or different injection fluids, and the surfactant flood can include additional or different surfactants and/or injection fluids.

At 1150, a second set of CT images of the core 130 are collected while performing the second core-flood test. The CT scanner system can monitor fluid imbibition from the fracture space 135 to the core 130. Fluid saturations of the core 130 can be determined based on the CT images. For example, CT images during the fluid injection, the water flood, and the surfactant flood phases can be obtained and analyzed, for example, to determine the fluid saturation during the respective phases (e.g., the brine saturation, the NaBr saturation, decane saturation during the respective injection phases, decane saturation during the water flood, decane saturation during the surfactant flood, etc.).

FIGS. 13A-F are 3D CT images showing decane saturation history of a core 130 during surfactant injection in an imbibition test. As shown in FIGS. 13A-F, the injected surfactant solution imbibes from around the core 130 and no front is observed.

At 1160, fluid saturations of the core 130 are analyzed based on the first set of CT images and the second set of CT images, for example, according to the techniques described with respect to Eqs. (1)-(5). In some implementations, the CT numbers, pore volume (PV), pore volume injected (PVI), porosity, or other parameters related to the saturation of the core 130 can be determined. Recovery factor (RF), incremental recovery factor (IRF), or other metrics for evaluating the effectiveness of oil recovery techniques (e.g., effectiveness of the surfactant flood, the reduction of IFT) can be derived based on the core-saturation parameters.

At 1170, the core 130 can be cleaned. To clean the core 130, the confining pressure can be re-applied and cleaning fluids (e.g., toluene, isopropanol) are injected.

Figure 14:
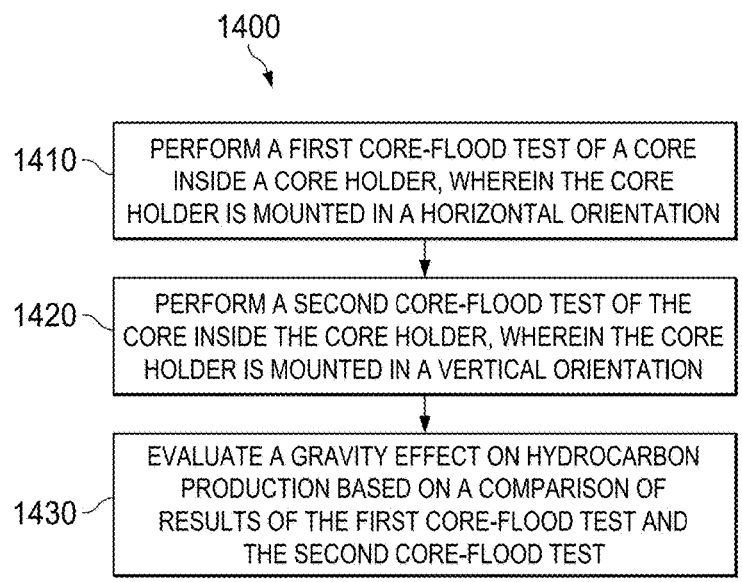
FIG. 14 is a flow chart showing another example process for operating the example core-flood test system.
Figure 12C:
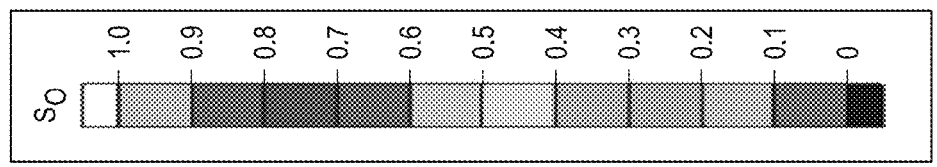
FIGS. 12A-F are example three-dimensional (3D) CT images showing decane saturation history of a core during a saturation test.
Figure 12C:
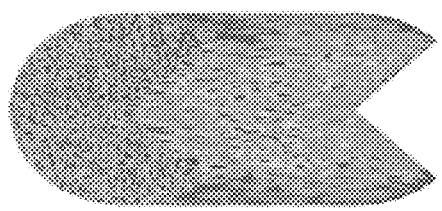
Figure 12B:
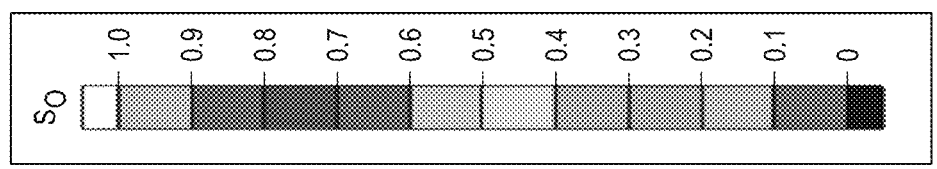
Figure 12B:
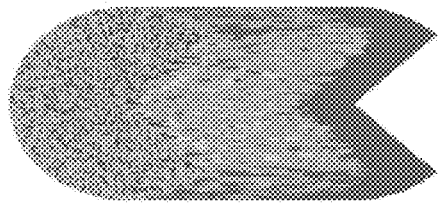
Figure 12A:
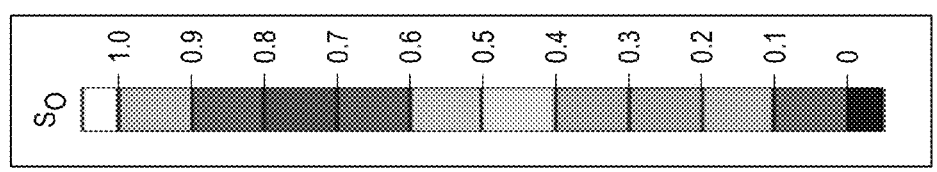
Figure 12A:
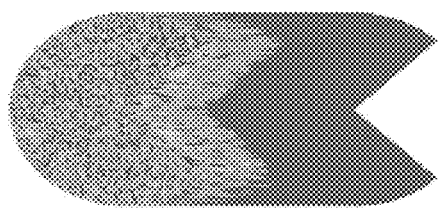
Figure 12F:
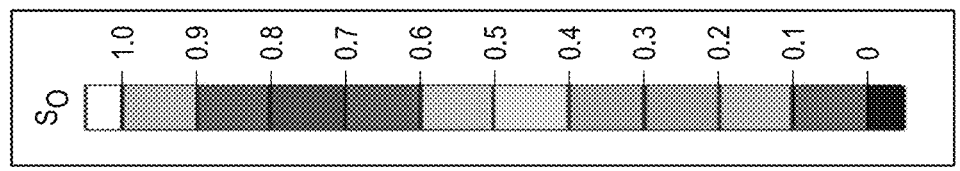
Figure 12F:
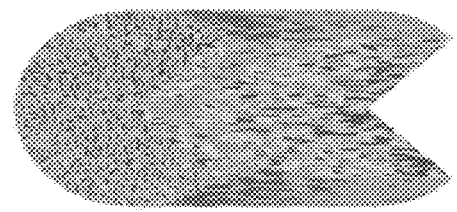
Figure 12E:
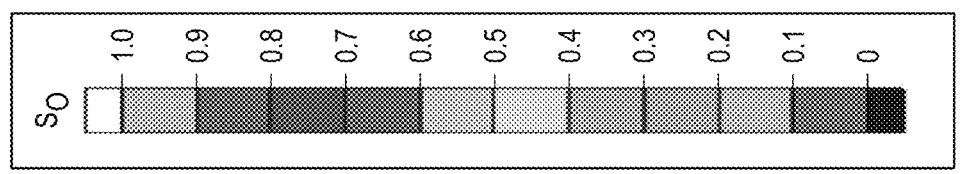
Figure 12E:
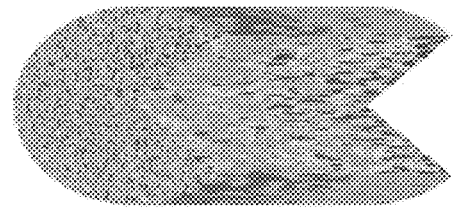
Figure 12D:
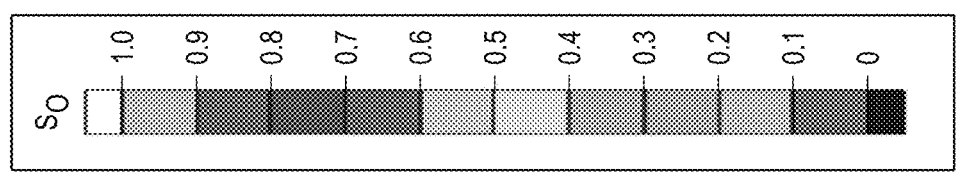
Figure 12D:
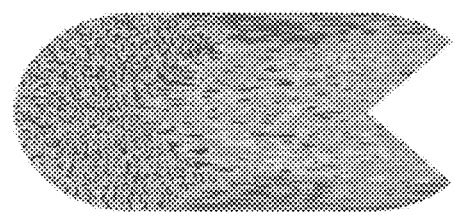
Figure 13C:
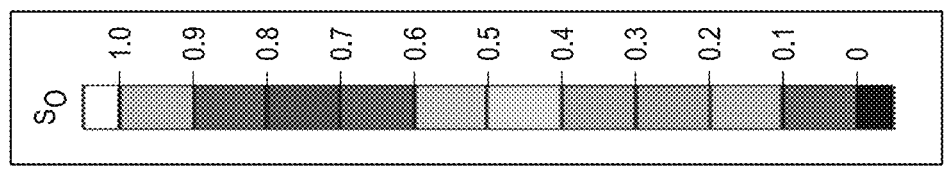
FIGS. 13A-F are 3D CT images showing decane saturation history of a core during surfactant injection in an imbibition test.
Figure 13C:
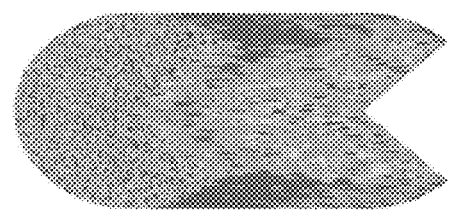
Figure 13B:
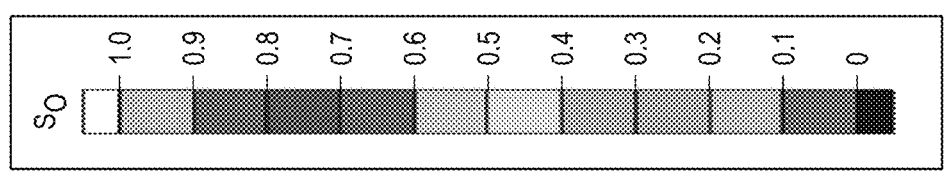
Figure 13B:
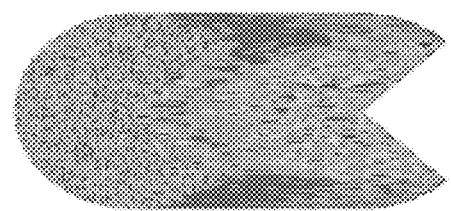
Figure 13A:
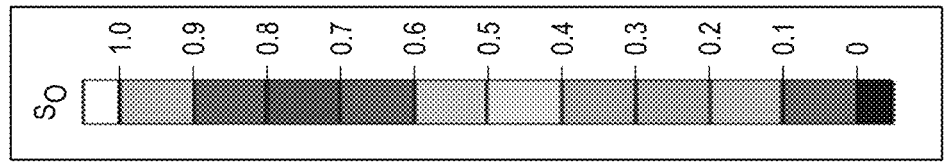
Figure 13A:
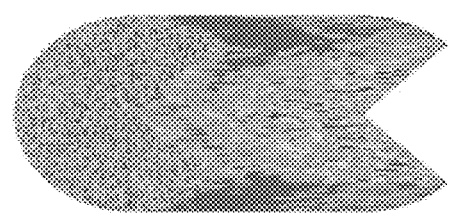
Figure 13D:
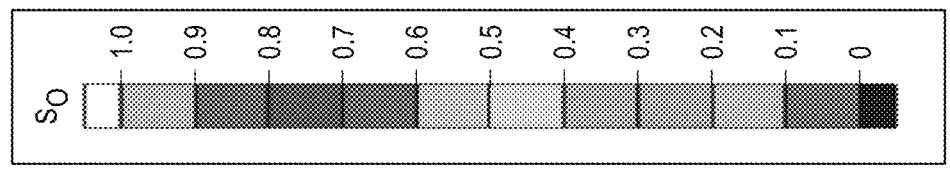
Figure 13D:
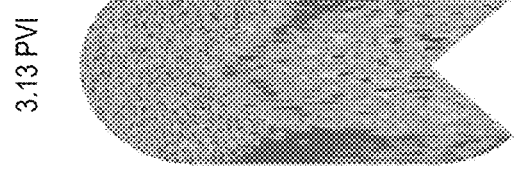
Figure 13E:
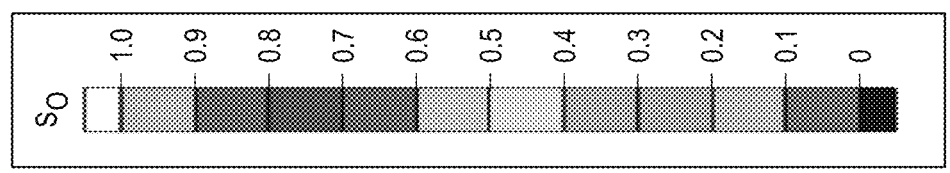
Figure 13E:
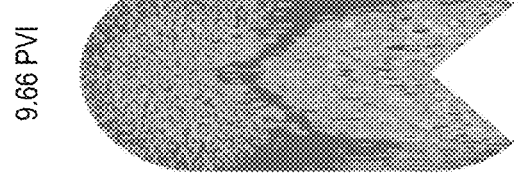
Figure 13F:
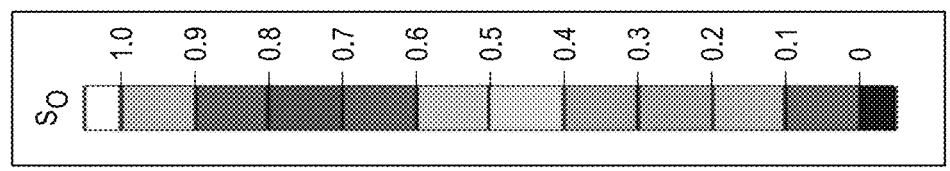
Figure 13F:
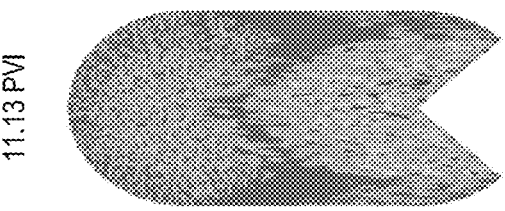

FIG. 14 is a flow chart showing an example process 1400 for operating the example core-flood test system 100, for example, to investigate gravity effects on oil recovery. As described above, the core holder 150 can be mounted horizontally or vertically on a positioning table. Experiments or tests can be conducted, for example, to investigate the effect of gravity on oil recovery when capillary forces are reduced in fractured systems. Horizontal experiments can be conducted as base cases to allow for quantifying the improvement in oil recovery due to gravity in the vertical experiments.

At 1410, a first core-flood test of a core inside a core holder 150 is performed, wherein the core holder 150 is mounted in a horizontal orientation. At 1420, a second core-flood test of the core inside the core holder 150 is performed, wherein the core holder 150 is mounted in a vertical orientation. At 1430, a gravity effect on hydrocarbon production is evaluated based on a comparison of results of the first core-flood test and the second core-flood test. In some instances, each of the first core-flood test and the second core-flood test can be conducted according to the example process 1100 described with respect to FIG. 11. For example, each of the horizontal test and the vertical test can include a saturation test and an imbibition test. CT images of the core 130 at different phases of the horizontal test and the vertical test can be collected.

Both tests can be conducted similarly except the orientation of the core holder 150. The same surfactant (e.g., NEODOL 25-3) can be used in both experiments. The effectiveness of the surfactants in IFT reductions in a gravity-assisted oil recovery can be assessed. In some implementations, the RF and/or IRF of the horizontal and vertical experiments with respect to the PVI can be compared. In some implementations, the analysis and evaluation can be performed manually or automatically, for example, by a computer system. In some implementations, the evaluated results can be output, for example, in text, table, graph, chart, or other format through one or more output devices (e.g., a graphic user interface on a display) of the computer system to a user.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A system for performing a core-flood test, the system comprising:
a core holder configured to be coupled to a computed tomography (CT) scanner system to monitor fluid saturations of a core comprising a rock sample; and
a core sleeve to be received in the core holder, the core holder and the core sleeve separated by a confining space, the core sleeve to receive the core, wherein the core sleeve is configured to contact the core in response to a confining pressure applied to the core sleeve in the confining space and to be separate from the core in response to the confining pressure being removed, creating a fracture space between the core and the core sleeve, and wherein the core is configured to receive injected hydrocarbon;
an injection plate attached to a first end of the core holder for transferring injected fluids to the core, the injection plate comprising an injection end cap tapered to substantially matching an inner diameter of the core sleeve for sealing the injection plate and the core sleeve; and a production plate attached to a second end of the core holder for collecting at least a portion of the hydrocarbon produced from the core.

2. The system of claim 1, further comprising a plurality of rods for connecting the injection plate, the production plate, and the core holder.

3. The system of claim 2, further comprising sealants applied around an edge of the core sleeve in contact with the injection plate and an edge of the core sleeve in contact with the production plate.

4. The system of claim 1, wherein each of the injection plate and the production plate comprises a distribution channel for uniformly distributing injected fluids into the core.

5. The system of claim 4, wherein the distribution channel further comprises an outer channel configured to transfer injected fluids to the fracture space between the core and the core sleeve.

6. The system of claim 1, wherein the injection plate comprises:
 a first injection port for transferring an injection fluid into the core; and
 a second injection port for transferring a confining fluid into the confining space.

7. The system of claim 1, wherein the production plate comprises a production port for transferring produced hydrocarbon.

8. The system of claim 1, wherein the core holder is made of polyvinyl chloride (PVC).

9. A system for performing a core-flood test, the system comprising:
 a core holder configured to be coupled to a computed tomography (CT) scanner system to monitor fluid saturations of a core comprising a rock sample; and
 a core sleeve to be received in the core holder, the core holder and the core sleeve separated by a confining space, the core sleeve to receive the core, wherein the core sleeve is configured to contact the core in response to a confining pressure applied to the core sleeve in the confining space and to be separate from the core in response to the confining pressure being removed, creating a fracture space between the core and the core sleeve; and
 an injection plate attached to a first end of the core holder for transferring injected fluids to the core, the injection plate comprising an injection end cap substantially matching an inner diameter of the core sleeve for sealing the injection plate and the core sleeve.

10. The system of claim 9, wherein the core is configured to receive injected hydrocarbon, and wherein the system further comprises a production plate attached to a second end of the core holder for collecting at least a portion of the hydrocarbon produced from the core.

11. A core-flood test method comprising:
 performing a first core-flood test of a core inside a core holder, wherein the core holder is mounted in a horizontal orientation;
 performing a second core-flood test of the core inside the core holder, wherein the core holder is mounted in a vertical orientation; and
 evaluating a gravity effect on hydrocarbon production based on a comparison of results of the first core-flood test and the second core-flood test.

12. The core-flood test method of claim 11, wherein each of the first core-flood test and the second core-flood test comprises a saturation test and an imbibition test.

13. The core-flood test method of claim 11, wherein performing the first core-flood test on the core inside the core holder comprises:
 collecting a first plurality of computed tomography (CT) images of the core while performing a third core-flood test;
 after performing the third core-flood test, performing a fourth core-flood test on the core using the core holder;
 collecting a second plurality of CT images of the core while performing the fourth core-flood test; and
 analyzing fluid saturations of the core based on the first plurality of CT images and the second plurality of CT images.

14. The core-flood test method of claim 13, wherein the third core-flood test comprises a saturation test and the fourth core-flood test comprises an imbibition test.

15. The core-flood test method of claim 13, further comprising,
 prior to performing the third core-flood test, collecting a CT image of the core to calculate porosity of the core.

16. The core-flood test method of claim 13, wherein performing the third core-flood test on the core comprises:
 applying a confining pressure;
 injecting brine into the core; and
 injecting a hydrocarbon fluid into the core.

17. The core-flood test method of claim 16, further comprising injecting $CO_2$ into the core before injecting the brine into the core.

18. The core-flood test method of claim 13, wherein performing the fourth core-flood test on the core comprises:
 releasing a confining pressure;
 injecting a hydrocarbon fluid into a fracture space between the core and a core sleeve;
 injecting brine into the core to mimic a water flood; and
 injecting a surfactant flood into the core.

* * * * *